United States Patent [19]

Odis

[11] 4,173,979
[45] Nov. 13, 1979

[54] URINE BAG COVER AND HOLDER DEVICE

[76] Inventor: Johnnie M. Odis, 4941 W. Washington Blvd., Chicago, Ill. 60644

[21] Appl. No.: 805,291

[22] Filed: Jun. 10, 1977

[51] Int. Cl.² ............................................. A61F 5/44
[52] U.S. Cl. ................................................... 128/295
[58] Field of Search ............................... 128/295, 283

[56] References Cited

U.S. PATENT DOCUMENTS

| 2,595,934 | 5/1952 | Ginsburg | 128/283 |
| 2,699,782 | 1/1955 | Chester | 128/295 |

FOREIGN PATENT DOCUMENTS

| 1445658 | 6/1966 | France | 128/295 |

Primary Examiner—Robert W. Michell
Assistant Examiner—M. A. Juten
Attorney, Agent, or Firm—Thomas R. Vigil

[57] ABSTRACT

The cover and holder device is made of a cloth material which is non-irritating to human skin and is adapted to provide a buffer between a reusable plastic urine bag which is irritating to human skin and the leg of a wearer thereof thereby to minimize discomfort to the person who needs to wear such a urine bag strapped to his/her leg. The device includes a bag portion with slits through which the straps of the bag extend and cloth straps aligned with the plastic urine bag straps to provide an underlay or buffer between them and the persons leg.

5 Claims, 4 Drawing Figures

URINE BAG COVER AND HOLDER DEVICE

BACKGROUND OF THE INVENTION

1. Field of the Invention

The present invention relates to a combined cover and holder device for a reusable urine bag. Such devices are presently classified in Class 128, Subclass 295 and related subclasses.

2. Description of the Prior Art

Heretofore various devices have been proposed for holding and/or covering liquid containing bags. Examples of covers and holders are disclosed in U.S. Pat. Nos. 718,053 and 1,025,012.

Also, there has been proposed a harness for a disposable urine bag which harness is designed to be strapped around the waist and leg and has a flat portion extending along the leg for holding a disposable urine bag. Such a harness is disclosed in U.S. Pat. No. 3,897,785.

Further, there has been proposed a pouch for a urine bag with mounting straps for mounting the pouch on a person's leg. Such an assembly is disclosed in French Pat. No. 1,445,658.

As will be explained in more detail hereinafter the present invention differs from these previously proposed devices for holding a reusable plastic urine bag by providing a combined cover and holder device for a reusable plastic urine bag which device, not only serves as a holder for the urine bag, but also provides a buffer or insulating layer of material between the reusable urine bag and the straps thereof and the persons leg on which it is strapped thereby to minimize irritation to the person's leg from the plastic material from which the disposable urine bag is made or from the residue of cleaning agents left on the bag after it is washed.

SUMMARY OF THE INVENTION

According to the invention there is provided for use in an assembly which includes a reusable urine bag which is made of a flexible material that is irritating to human skin and which has flexible mounting straps extending therefrom, an improved combination cover and holder device which is constructed of a cloth material made from a natural or synthetic fiber which is substantially non-irritating to human skin and which includes a generally rectangular shaped bag portion with an outer wall and an inner wall, each wall being secured along two opposite side edges thereof and along at least parts of a bottom edge thereof to the adjacent other wall, the adjacent side edges of the walls along the top edge of the bag portion being unattached along a major portion their length to define an opening therebetween for receiving the reusable urine bag, said inner wall having two pairs of spaced apart slits, each slit being aligned with the connection of one of the mounting straps of the urine bag to the urine bag and said device further including two pairs of straps, each strap having a free outer end and an inner end which is secured to the outer surface of said inner wall adjacent one of said slits and each strap being in a position to extend partially around a human leg and between the leg and one of the urine bag mounting straps.

Further according to the invention there is provided in combination, a reusable urine bag which is made of a flexible material that is irritating to human skin and which has flexible mounting straps extending therefrom and an improved combination cover and holder device for said urine bag, said device being constructed of a cloth material made from a natural or synthetic fiber which is substantially non-irritating to human skin and including a generally rectangular shaped bag portion with an outer wall and an inner wall, each wall being secured along two opposite side edges thereof and along at least part of the bottom edge thereof to the adjacent other wall, the adjacent side edges of the walls along the top edge of the bag portion being unattached along a major portion of their length to define an opening therebetween for receiving said reusable urine bag, said inner wall having two pairs of spaced apart slits, each slit being aligned with a connection of one of said mounting straps of said urine bag to said urine bag and said device further including two pairs of straps, each strap having a free outer end and an inner end which is secured to the outer surface of said inner wall adjacent one of said slits and each strap being in a position to extend partially around a human leg and between the leg and one of said urine bag mounting straps.

DESCRIPTION OF THE PREFERRED EMBODIMENT

Figure 1:
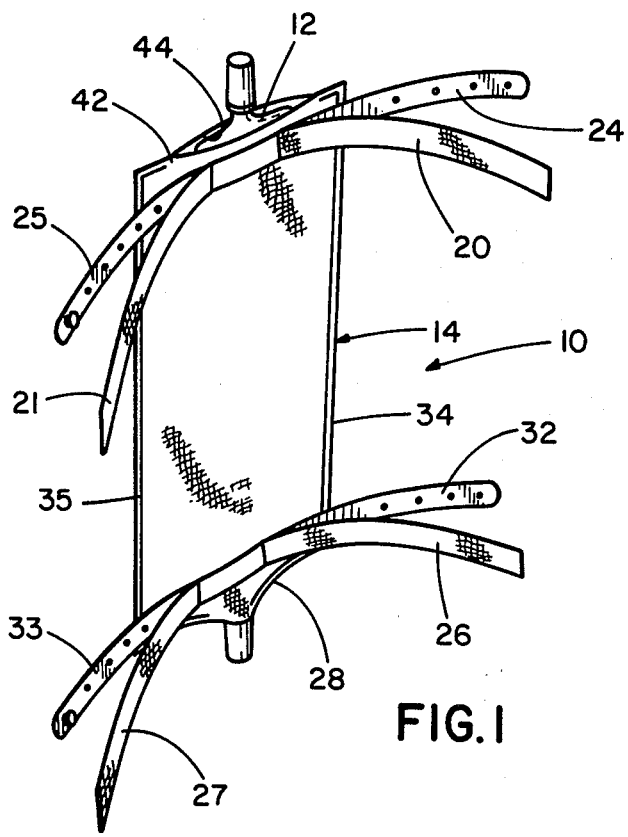
FIG. 1 is a perspective view of the urine bag cover and holder dvice of the present invention with a reusable urine bag therein.

Referring now to the drawings in greater detail, there is illustrated in FIG. 1 a combined cover and holder device made in accordance with the teachings of the present invention and generally identified by the reference numeral 10. The device 10 is especially adapted for receiving, covering, holding and mounting a reusable plastic urine bag 12 on a person's leg. These urine bags are worn by persons who have limited or no control over the evacuation or release or urine such as a person with a spinal injury, e.g., a quadriplegic.

Figure 3:
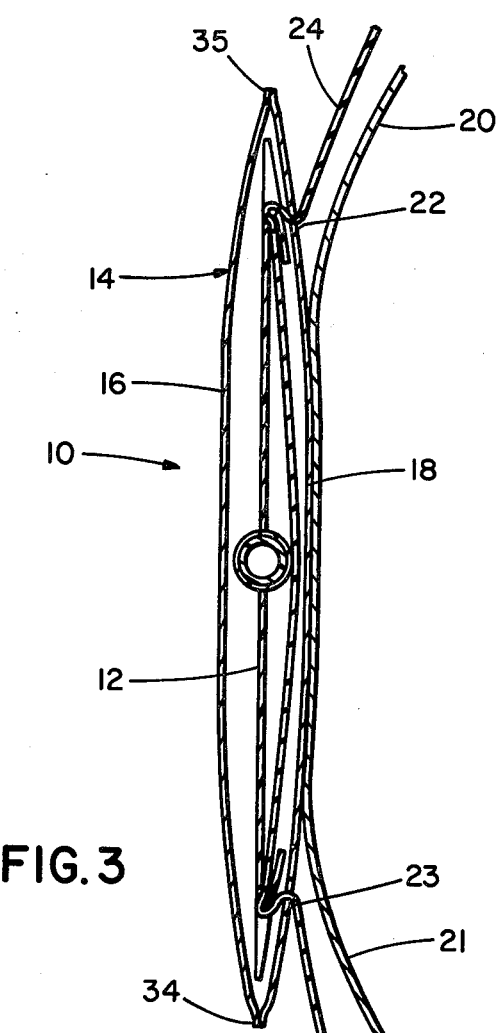
FIG. 3 is a horizontal sectional view taken along line 3—3 of FIG. 2.
Figure 2:
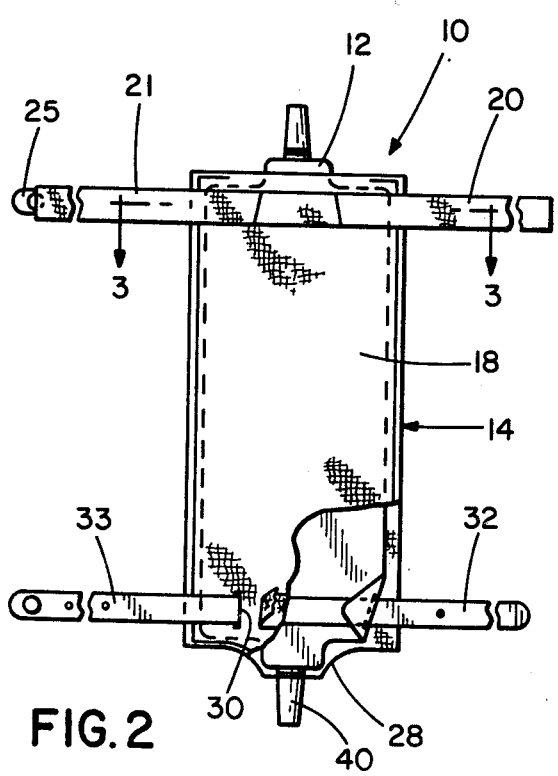
FIG. 2 is a vertical plan view of the urine bag cover and holder device shown in FIG. 1 with portions thereof folded outwardly and broken away.
Figure 4:
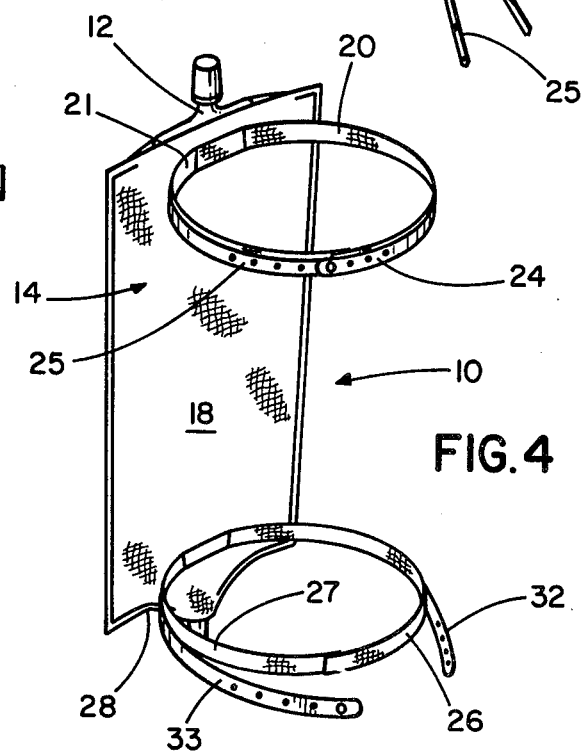
FIG. 4 is a vertical perspective view of the urine bag cover and holder device showing how it would be fitted around a person's leg.

The device 10 includes a bag portion 14 in which the urine bag 12, is received and, as best shown in FIG. 3, the bag portion 14 has an outer wall 16 and an inner wall 18. An upper pair of straps 20 and 21 are secured to the outer surface of the inner wall 18 and extend outwardly therefrom adjacent slits 22 and 23 formed in the inner wall 18 through which plastic straps 24 and 25 of the reusable plastic urine bag 12 can extend, as best illustrated in FIG. 3. A lower second pair of straps 26 and 27 also extend from the outer surface of the inner wall 18 of the bag portion 14 adjacent the bottom side 28 of the bag portion 14 and adjacent slits, such as slit 30 (FIG. 2), through which lower plastic straps 32 and 33 of the urine bag 12 can extend.

The inner and outer walls 16 and 18 of the bag portion 14 are secured together along adjacent edges of opposite sides 34 and 35 of the bag portion 14. Also the adjacent edges of walls 16 and 18 along the bottom side 28 of the bag portion 14 are unattached along a portion of the length thereof midway between the bottom corners of the bag portion 14 to provide an opening for a lower nozzle 40 of the urine bag 12.

The upper side 42 of the bag portion 14 has only a small portion of the adjacent edges of walls 16 and 18 secured together at the upper corners of the bar portion 14 so as to provide a sufficiently large opening 44 for inserting the urine bag 12 into the bag portion 14.

In accordance with the teachings of the present invention the reusable urine bag cover and holder device 10 is made of a cloth material which is made from a natural or synthetic fiber which is substantially non-irritating to human skin. Examples of such materials are polyester or cotton materials or materials made from a blend or mixture of cotton and polyester fibers.

Also, the bag portion 14 and straps 20, 21, 26 & 27 are constructed and arranged so as to underly the urine bag 12 and the straps 24, 25, 32 & 33 thereof so as to provide a buffer or insulating layer between the urine bag and the straps thereof and a human leg on which the urine bag is attached. In this way, irritation of the skin of the leg is minimized, if not altogether eliminated.

In an emperical test of a reusable urine bag cover and holder device constructed in accordance with the teachings of the present invention, irritation, discomfort and chaffing was essentially completely eliminated for a quadriplegic who wore the cover and holder device with reusable urine bags held therein.

From the foregoing description it is apparent that the reusable urine bag cover and holder device of the present invention has several advantages, some of which have been described above and others of which are inherent in the invention. The major advantage is that with the cover and holder device 10 of the present invention, reusable urine bags can be utilized without the plastic material of the bag and straps and/or residue from strong cleaning solutions on the plastic material of the bag and straps irritating the skin of the wearer. Also the cover and holder device 10 can be made of different colored cloth materials to match or contrast with wearing apparel of the wearer thereby to reduce and minimize the unattractiveness of a translucent plastic urine bag strapped to a person's leg. Accordingly, the scope of the present invention is only to be limited as necessitated by the accompanying claims.

I claim:

1. For use in an assembly which includes a reusable urine bag which is made of a flexible material that is irritating to human skin and which has flexible mounting straps extending therefrom, an improved combination cover and holder device which is constructed of a cloth material made from a natural or synthetic fiber which is substantially non-irritating to human skin and which includes a generally rectangularly shaped bag portion with an outer wall and an inner wall, each wall being secured along two opposite side edges thereof and along at least parts of a bottom edge thereof to the adjacent other wall, the adjacent side edges of the walls along the top edge of the bag portion being unattached along a major portion of their length to define an opening therebetween for receiving the reusable urine bag, said inner wall having two pairs of spaced apart slits, each slit being aligned with the connection of one of the mounting straps of the urine bag to the urine bag and said device further including two pairs of straps, each strap having a free outer end and an inner end which is secured to the outer surface of said inner wall adjacent one of said slits and each strap being in a position to extend partially around a human leg and between the leg and one of the urine bag mounting straps.

2. The device according to claim 1 being made of a polyester material.

3. The device according to claim 1 being made of cotton.

4. The device according to claim 1 being made of cotton and polyester fibers.

5. In combination, a reusable urine bag which is made of a flexible material that is irritating to human skin and which has flexible mounting straps extending therefrom and an improved combination cover and holder device for said urine bag, said device being constructed of a cloth material made from a natural or synthetic fiber which is substantially non-irritating to human skin and including a generally rectangular shaped bag portion with an outer wall and an inner wall, each wall being secured along two opposite side edges thereof and along at least part of the bottom edge thereof to the adjacent other wall, the adjacent side edges of the walls along the top edge of the bag portion being unattached along a major portion of their length to define an opening therebetween for receiving said reusable urine bag, said inner wall having two pairs of spaced apart slits, each slit being aligned with a connection of one of said mounting straps of said urine bag to said urine bag and said device further including two pairs of straps, each strap having a free outer end and an inner end which is secured to the outer surface of said inner wall adjacent one of said slits and each strap being in a position to extend partially around a human leg and between the leg and one of said urine bag mounting straps.

* * * * *